United States Patent
Gagliardoni et al.

(10) Patent No.: US 9,943,681 B2
(45) Date of Patent: Apr. 17, 2018

(54) ANTI-FREE-FLOW VALVE

(71) Applicant: Cedic S.R.L., Peschiera Borromeo (MI) (IT)

(72) Inventors: Giancarlo Gagliardoni, Caracas (VE); Jan Williem Marinus Mijers, Haarlem (NL)

(73) Assignee: Cedic S.R.L. (IT)

( * ) Notice: Subject to any disclaimer, the term of this patent is extended or adjusted under 35 U.S.C. 154(b) by 159 days.

(21) Appl. No.: 14/762,160

(22) PCT Filed: Jan. 18, 2013

(86) PCT No.: PCT/EP2013/050882
§ 371 (c)(1),
(2) Date: Jul. 20, 2015

(87) PCT Pub. No.: WO2014/111150
PCT Pub. Date: Jul. 24, 2014

(65) Prior Publication Data
US 2015/0367121 A1   Dec. 24, 2015

(51) Int. Cl.
*A61M 39/26* (2006.01)
*A61M 39/28* (2006.01)
(Continued)

(52) U.S. Cl.
CPC .......... *A61M 39/26* (2013.01); *A61J 15/0076* (2015.05); *A61J 15/0092* (2013.01);
(Continued)

(58) Field of Classification Search
CPC .............. A61M 39/26; A61M 5/14228; A61M 5/14232; A61M 5/16881; A61M 39/281;
(Continued)

(56) References Cited

U.S. PATENT DOCUMENTS 5,370,427 A    12/1994  Hoelle et al.
6,039,302 A *  3/2000   Cote, Sr. .............. A61M 39/26
                                              251/149.1
(Continued)

FOREIGN PATENT DOCUMENTS

WO    2006/015301    2/2006
WO    2013/010580    1/2013

OTHER PUBLICATIONS

International Search Report and Written Opinion, PCT/EP2013/050882, Cedic S.R.L., dated Jul. 19, 2013.

*Primary Examiner* — Laura Bouchelle
(74) *Attorney, Agent, or Firm* — Jansson Munger McKinley & Kirby Ltd.

(57) ABSTRACT

An anti-free-flow valve for use with an enteral feeding or infusion pump is disclosed. The valve includes a first component connectable to a first tube and has a first cavity and a sealing element and a second component adapted to be connected to the first component and a second tube and having a second cavity, a valve seat and a flexible portion. The sealing element and the valve seat are sealingly engageable to control fluid flow between the first and second cavities. The valve is configured such that applying an axial tension force between the first and second components brings the valve into an open position. The second component's flexible portion includes a bellows which has a spring function in the axial direction and a housing at least partially covering the second component and configured to operate as a stop limiting the axial movement of the second component.

14 Claims, 6 Drawing Sheets

(51) Int. Cl.
*F16K 7/02* (2006.01)
*A61M 5/142* (2006.01)
*A61J 15/00* (2006.01)
*A61M 5/168* (2006.01)
*F16K 1/36* (2006.01)
*F16K 27/02* (2006.01)
*F16K 27/10* (2006.01)
*A61M 39/24* (2006.01)

(52) U.S. Cl.
CPC .... *A61M 5/14228* (2013.01); *A61M 5/14232* (2013.01); *A61M 5/16881* (2013.01); *A61M 39/281* (2013.01); *F16K 1/36* (2013.01); *F16K 7/02* (2013.01); *F16K 27/02* (2013.01); *F16K 27/102* (2013.01); *A61M 2039/2433* (2013.01); *A61M 2039/268* (2013.01); *A61M 2205/0216* (2013.01); *A61M 2207/00* (2013.01)

(58) Field of Classification Search
CPC .... A61M 2039/2433; A61M 2039/268; A61M 2205/0216; A61M 2207/00; A61M 2039/267; A61M 2039/226; A61M 39/24; A61M 2039/2446; A61M 2039/2473; A61M 39/261; A61M 39/268; A61M 39/10; A61M 39/22; A61M 2039/1072; A61J 15/0076; A61J 158/0092; F16K 1/36; F16K 7/02; F16K 27/102; Y10T 137/7879; Y10T 137/7888; Y10T 137/7895
USPC ...... 251/319–323, 331–333, 149.8; 137/843, 137/852, 849, 535
See application file for complete search history.

(56) References Cited

U.S. PATENT DOCUMENTS

| | | | |
|---|---|---|---|
| 6,224,578 B1* | 5/2001 | Davis | A61M 5/1411 604/247 |
| 7,837,658 B2* | 11/2010 | Cote, Sr. | A61M 39/045 251/149.6 |
| 2003/0229309 A1* | 12/2003 | Babkes | A61M 39/281 604/131 |
| 2011/0125103 A1* | 5/2011 | Rondeau | A61M 5/1411 604/251 |

* cited by examiner

ANTI-FREE-FLOW VALVE

RELATED APPLICATION

This application is a national stage application of PCT Application No. PCT/EP2013/050882 filed Jan. 18, 2013, the entire contents of which are incorporated herein by reference in its entirety.

FIELD OF THE INVENTION

This invention relates to anti-free-flow tube valves for use with enteral feeding pumps adapted to feed nutritionals or with infusion pumps adapted to infuse medical solutions to patients. More particularly, this invention relates to tube valves connected to a tube which may be fitted to enteral feeding sets or infusion sets and the like, in which the tube valve prevents free-flow of enteral formula through the enteral feeding set or of solutions through the infusion set unless the tube with the tube valve is properly mounted to an enteral feeding pump or infusion pump.

BACKGROUND OF THE INVENTION

The use of infusion and feeding sets to administer solutions and food to a patient is well known in medical arts. Infusion and enteral sets are used for both enteral and parenteral application, respectively. For hygienic reasons the infusion and enteral sets must be disposed of immediately after use, making it single-use equipment which may be recycled afterwards. Enteral feeding pumps are used to provide the patient with nutrition and medication (formula) when they are unable, for a variety of reason, to eat normally. Parenteral (intravenous) solutions are provided to patients to ensure adequate hydration and to provide needed nutrients, minerals or medication. Often, the enteral or infusion set is placed in a free standing arrangement in which gravity forces the formula or solution into the patient. The rate at which the solution enters the patient can be roughly controlled by various clamps, such as roller clamps, which are currently available on the market.

In many applications, it is necessary to precisely control the amount of solution or formula which enters the patient. When this is the case, a regulating device such as an infusion pump, is placed along the infusion set to control the rate at which the solution is fed to the patient. In applications where a pump etc. is used the clamps or valves used to regulate flow are typically open to their fullest extent to prevent the clamp or valve from interfering with the proper functioning of the pump. The clamp or valve is opened with the expectation that the enteral feeding pump or infusion will control fluid flow through the enteral or infusion set. However, emergencies or other distractions may prevent the medical personnel from properly loading the enteral or infusion sets in the enteral feeding pump or the infusion pump. Furthermore, the enteral or infusion sets may be inadvertently dislodged from the pump during operation of the pump.

In many enteral feeding systems the engagement of the pump tube to the rotor controls the flow of fluid to the patient according to the speed of the rotor (peristaltic pump). In the event the enteral feeding set is not properly mounted to the pump, an excess flow of fluid through the feeding set can occur under force of gravity known as free-flow often develops which is highly undesirable. Under a free-flow condition, an amount of solution or formula many times the desired dose can be supplied to the patient within a relatively short time period. This can be particularly dangerous if the solution contains potent medicine or the patient's body is not physically strong enough to adjust to the large inflow of solution or formula.

U.S. Pat. No. 6,224,578 discloses a valve device which is incorporated into the lower portion of a drip chamber for preventing the free flow of fluid through a tube assembly when the tube assembly is disengaged from a pump of a fluid administration system, while permitting fluid flow when the tube assembly is engaged around a rotor of the pump. The valve device comprises a valve body having a top component sealingly engaged with a bottom component. The top component is integrally formed with the lower portion of the drip chamber and defines a plurality of axial fluid passageways formed around a stationary plunger which seals against a opening formed at the upper portion of the bottom component. The opening is in communication with a lumen that extends into a hollow tube assembly which is attached to the bottom component of the valve body. The bottom component further includes a flex joint made of a flexible material that is adapted to flex and pull the opening away from the plunger to establish fluid flow through the valve device. In operation, a user applies a tensile force along the tube assembly by engaging the tube assembly around a rotor of a pump which pulls the flex joint away from the plunger and opens the valve device to fluid flow therethrough by gravity. When the tube assembly is disengaged from the rotor the flex joint is forced back to its original position such that the plunger is sealed against the opening, thereby preventing fluid free-flow through the fluid administration system. The '578 patent comprises the features of the preamble of claim 1 of the present invention.

United States Published Patent Application 2003/0229309 describes an anti-free-flow device for a fluid administration system having a tube assembly engageable with a pump with one end of the tube assembly connected to a source of fluid and the other end in fluid flow communication with a patient. The valve device comprises a tube portion defining a channel in-line along a portion of the tube assembly and a body disposed and securely retained inside the channel. Fluid flow is allowed through the tube assembly whenever the tube assembly is in a stretched condition, such as when the tube assembly is engaged with the pump. However, fluid free-flow is prevented whenever the tube assembly is in a relaxed condition or disengaged from the pump.

The anti-free-flow devices of the known kind as describe above suffer from a number of disadvantages such as the fact that they tend to block the rather viscous enteral nutrition fluids which may contain a high percentage of fibres. This is due to the fact that the lumina of the valves are too small so that fibres may get stuck in the small openings and lumina. Thus, in many cases the use of anti free-flow valves in enteral feeding systems has been avoided whereby the necessary safety measures have been neglected.

Further, the handling of the silicone tubing in a peristaltic pump is related with high stretching or tensional forces of an AFF valve. Most of the prior art valves reduce the lumen for the fluid flow thus increasing the tendency to block viscous enteral nutrition fluids. Thus, there is a need for an anti free-flow device that overcomes some of the above-mentioned disadvantages of the prior art.

It is therefore the object of the present invention to provide a valve for engaging with a tube to be used in an enteral feeding or infusion pump which withholds over-stretching forces of the tubing, is simple in structure and small in size, reliable in function, easy to handle and compatible with the majority of existing pump devices, in particular peristaltic pumps. This object is achieved by the combination of features of the claimed invention. Particularly advantageous embodiments of the invention are subjects of the dependent claims.

SUMMARY OF THE INVENTION

According to the invention, a valve for engaging with a tube to be used in an enteral feeding or infusion pump adapted to feed a fluid to a patient comprises: a first component being adapted to be connected to a first tube and having a first cavity and a sealing element, a second component being adapted to be connected to the first component and a second tube, the second component having a second cavity, a valve seat and a flexible portion, wherein the sealing element of the first component and the valve seat of the second component are sealingly engageable for controlling fluid flow between the first and the second cavity, wherein applying an axial tension force between the first component and the second component will bring the valve into an open position, wherein the flexible portion comprises at least one bellows having a spring function in the axial direction, and a housing is provided at least partially covering the second component, wherein the housing is configured to operate as a stop limiting the movement of the second component.

The bellows with the spring function works in the axial direction so that applying a tensional force will not reduce the inside volume of the valve which is the critical factor for letting rather viscous fluids pass through the valve smoothly. Furthermore, the housing provides a stop for the stretching of the silicone tubing thus ensuring the normal function of the valve, and also provides protection for the sensitive bellows and valve seat areas.

Preferably, the first component, the second component and housing are rotationally symmetric and aligned along a common axis.

Advantageously, the first component and the housing are connected such that one end of the second component which may be formed as a ring is firmly engaged therebetween. A connection between the first component and the housing clamps or squeezes the second component firmly between those two elements such that any direct fixation of the second component to the first component or the housing is obsolete. This enables a simple construction and easier production process.

Preferably, the first component and the housing are connected by mechanical fasteners, welding, or bonding, preferably by ultrasonic welding. A mechanical fastener could be a ring which keeps both elements in tight fit connected with each other. However, ultrasonic welding is the preferred means of attachment because it ensures a solid and reliable connection and can be easily and exactly applied to such small parts. Ultrasonic welding facilitates very short welding periods and is highly economical.

It is also preferred that the first component and the housing are formed of relatively hard thermoplastic polymer material such as acrylonitrile butadiene styrene (ABS), polypropylene (PP), polyvinyl chloride (PVC), polyethylene (PE) or any combination thereof. Further, the second component may be formed of relatively soft thermoplastic elastomer (TPE) or silicone rubber material. The use of thermoplastic elastomers and silicone rubber in medical appliances is very common as those materials fulfil the hygienic requirements and can be handled in mass production. Further, the above-mentioned technologies relating to welding, bonding and fastening are common practice for the mentioned types of material.

Preferentially, the sealing element comprises a dome-shaped configuration with a plurality of side channels enabling fluid flow from the first cavity to the second cavity. It is preferred that the valve seat comprises a recess for snugly fitting with the dome-shaped sealing element. A circular, dome-shaped configuration of the sealing element with the corresponding fitting dimensions of the valve seat ensures a sufficient closure of the valve even when a slight torque is applied on the valve. The side channels are generally large enough to let fibrous material in the fluid pass. The shape of the channels can be adapted accordingly; i.e., the channels may have a rectangular, oval, square, triangular, polygonal or other suitable cross-sections which facilitate the stream of fluid therethrough.

The second component may be integral with the second tube. This avoids an additional gluing or connecting step and reduces the number of components.

Preferably, the valve comprises a flange to be fitted to a peristaltic pump. The flange which is preferably formed by the housing and the first component provides that the movement of the second component which is responsible for the opening and closing of the valve can be performed without any obstruction.

BRIEF DESCRIPTION OF THE DRAWINGS

The above object, features and advantages of the present invention will become apparent from a consideration of the following detailed description presented in connection with the accompanying drawings in which.

DETAILED DESCRIPTION OF PREFERRED EMBODIMENTS

Figure 1:
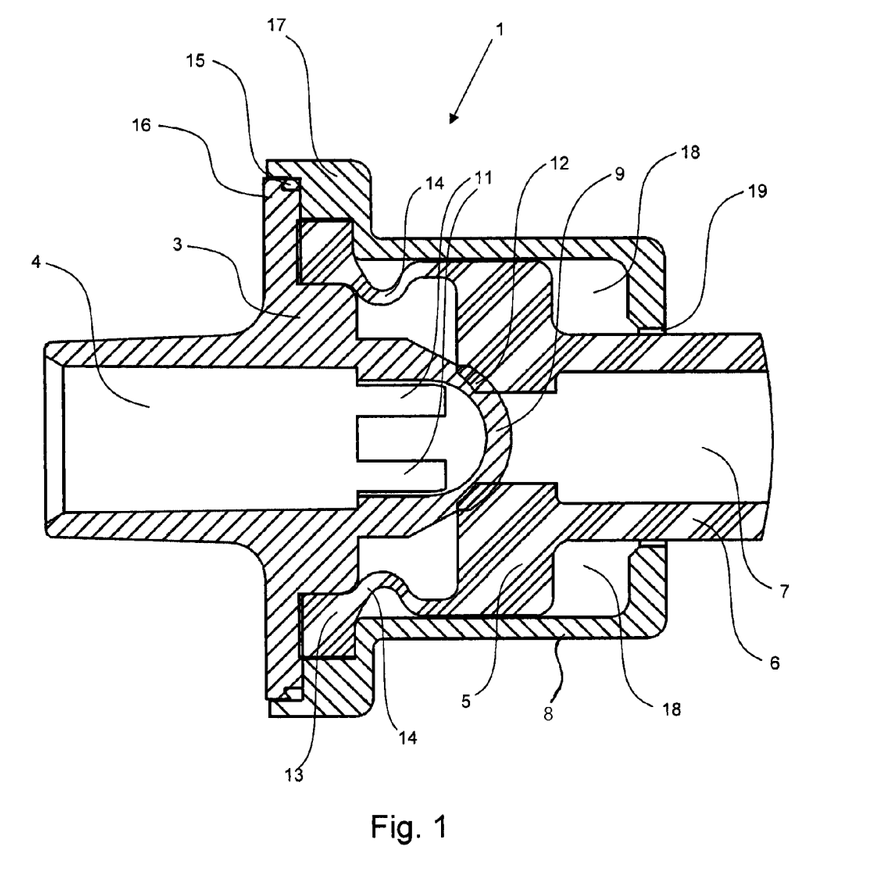
FIG. 1 is a sectional view of a preferred embodiment of the valve according to the invention.

FIG. 1 shows a sectional view of a preferred embodiment of the valve 1 according to the invention. Valve 1 comprises a first component 3 adapted to be connected to a first tube (not shown) and adapted to allow flow of fluid through a first cavity 4, a second component 5 being integral with a second tube 6 and having a second cavity 7, and a housing 8 enclosing the majority of second component 5.

First component 3 includes at its closed end a sealing element 9 which in the shown preferred embodiment comprises a dome-shaped configuration for an optimal fit with its counterpart. First component 3 also comprises channels 11 which enable fluid flow out of first cavity 4 into second cavity 7 which will later be described in more detail.

Second component 5 comprises inside a valve seat 12 which shows a mating surface corresponding to dome-shaped sealing element 9. Second component 5 further comprises at its outer end (left-hand side in FIG. 1) a ring 13 which is connected to the remainder of second component 5 by a bellows portion 14.

In the shown embodiment, the majority of first component 3 and particularly second component 5 are surrounded by housing 8 which is connected to first component 3 on one side and on the other side comprises an opening 19 through which second tube 6 passes. First component 3 and housing 8 are welded to each other by a welded joint 15, thereby clamping or engaging ring 13 of second component 5 firmly between each other.

Figure 2:
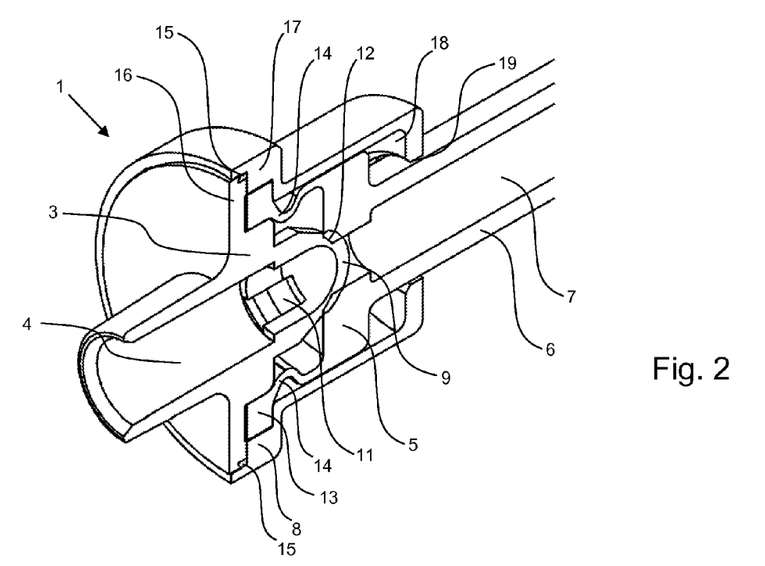
FIGS. 2 and 3 are perspective sectional views of the valve shown in FIG. 1 in the closed and open conditions, respectively.

Valve 1, as shown in FIG. 1, is in the closed configuration as can easily be seen because sealing element 9 is firmly sitting on valve seat 12 thereby blocking any flow of fluid from first cavity 4 to second cavity 7 or vice versa. In the preferred embodiment, second component 5 is formed of silicone rubber material, the same material as silicone tubing 6. Since first component 3 and housing 8 are preferably made of a thermoplastic polymer material which is relatively hard compared with the silicone rubber material of second component 5, valve seat 12 subsides a little upon pressing sealing element 9 in the axial direction. In the illustrated configuration, bellows 14, which has a spring-like function for the valve according to the invention, is in the relaxed position having an S-shape between ring 13 and the main body of second component 5. In this position, the spring force of the bellows 14 is just sufficient to press sealing element 9 slightly onto resilient valve seat 12 in order to provide an adequate seal. FIG. 2 shows a perspective sectional view of the valve of FIG. 1 in the same closed configuration. Since the majority of components have already been explained with respect to FIG. 1, unnecessary repetition is omitted. In addition to the above explanations, it can be seen that first component 3 comprises a first flange 16 which is connected with a second flange 17 of second component 5 having a welded joint 15 in between which is preferably executed by ultrasonic welding. Other methods of attaching first component 3 to housing 8 are possible; however, ultrasonic welding has proven very reliable and suitable for the valve according to the invention.

In the closed condition illustrated in FIGS. 1 and 2, a flow of fluid of first cavity 4 to second cavity 7 or vice versa is prohibited by sealing element 9 pressed upon and being engaged with valve seat 12 of second component 5. This means that fluid streaming from the left-hand side from the first tube into first cavity 4 will also flow through the channels 11 in first component 3 and fill the lumen formed between the left part of second component 5 and first component 3. The engagement of sealing element 9 with valve seat 12 forms a barrier for any fluid which is intended to flow from first cavity 4 on the left side to second cavity 7 on the right side of the valve depicted in FIGS. 1 and 2. In those drawings, it can also be seen that there is a lumen 18 between the outer side of second component 5 and the inner area of housing 8 so that second tube 6, which is integral with second component 5, may be moved in the axial direction away from first component 3 by the distance which equals the width of lumen 18.

Figure 3:
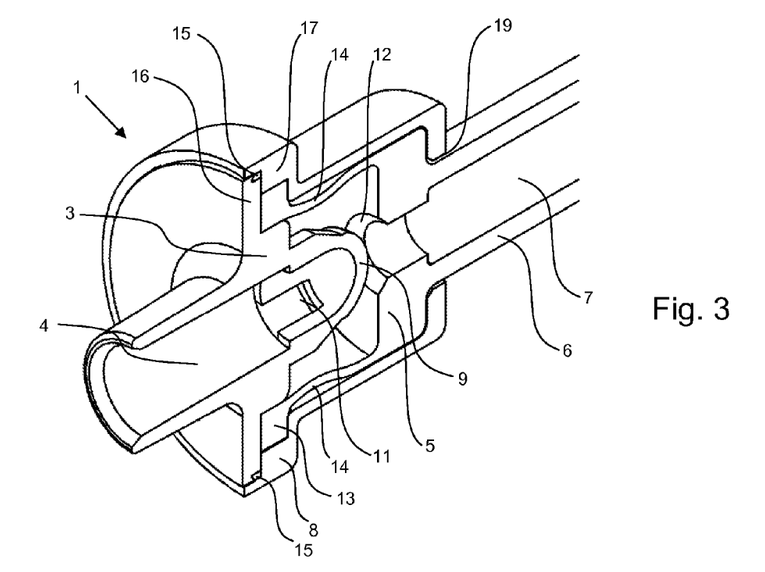

FIG. 3 shows a perspective sectional view of the valve of FIG. 1 in the open configuration. Again, unnecessary repetition of the description of the majority of components is omitted at this point since it is in the detailed description above. In order to open valve 1 as shown in FIG. 3, second tube 6 together with the majority of elements of second component 5 has been moved axially away from first component 3 such that sealing element 9 is now disengaged from valve seat 12 allowing fluid flow from first cavity 4 to second cavity 7 or vice versa. In other words, a pulling force has been applied to second tube 6 so that second component 5 is pulled away from first component 3. In this open configuration, valve 1 has been fully opened until the stop has been reached which is represented by the end of housing 8 which prevents second component 5 from being moved further beyond housing 8. In the open position lumen 18 has shrunk almost completely, and bellows 14 has been stretched such that the S-shape of the bellows has been substantially flattened out and is now almost straight. The stop has also a protective function; more specifically, once valve 1 is fully opened by pulling second tube 6 away from first component 3 in the axial direction, an additional pulling force in the same direction will not influence second component 5, i.e., those elements inside housing 8. Thus, it is possible to further stretch second tube 6, e.g., for attaching it to a peristaltic pump or to a cassette system of an infusion pump, but this further stretching will not negatively influence the function of the valve since it is protected by housing 8.

Figure 4:
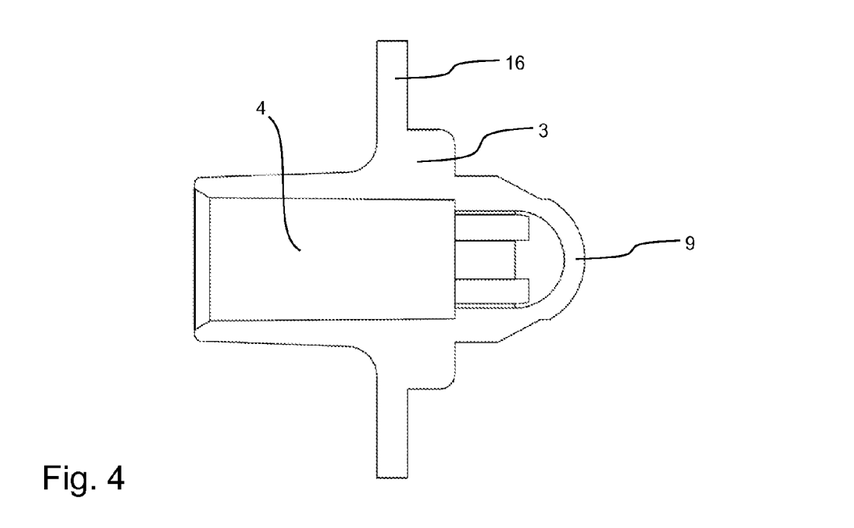
FIG. 4 is a sectional view of the first component of the preferred embodiment of the valve according to the invention.

FIG. 4 shows a section view of the first component of the preferred embodiment of the valve according to the invention. The elements of first component 3 have already been explained with reference to the previous figures. It should be noted that the configuration of sealing element 9 may be changed from the dome-like shape in the preferred embodiment to other shapes, e.g., a circular flat shape with a corresponding flat valve seat having a protrusion to form a suitable sealing. However, it has been found that the dome-shape of sealing element 9 with a corresponding negative (complementary) shape of valve seat 12 of second component 5 shows optimal sealing and fluid flow results.

Figure 5:
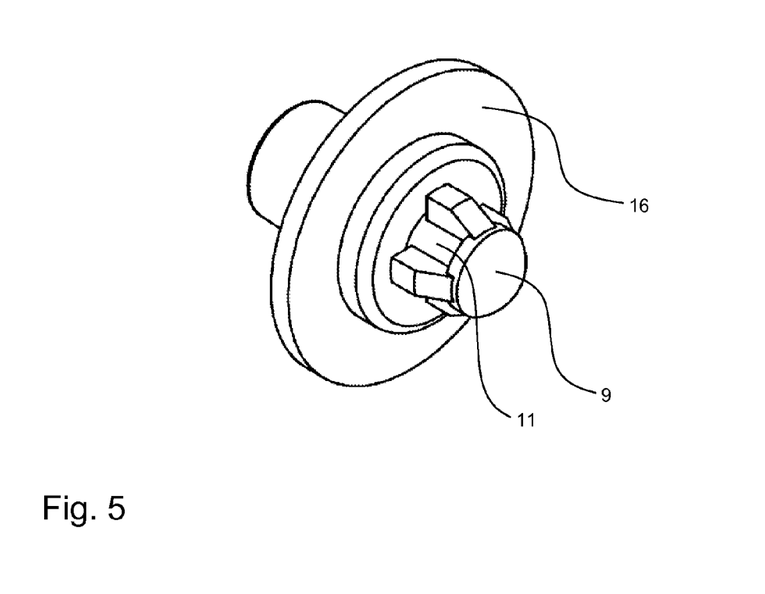
FIG. 5 is a perspective view of the first component of the preferred embodiment of the valve according to the invention.

FIG. 5 is a section view of the first component of the preferred embodiment of the valve according to the invention. Here it should be noted that the number of channels 11 is four in the preferred embodiment, but other numbers of channels could also be selected. It should be taken into account that the protrusion formed by the dome-shaped sealing element 9 should have a minimal stability. Thus, the number of channels cannot be increased too much because the remaining supporting elements supporting the valve seat must show the necessary torsional stability.

Figure 6:
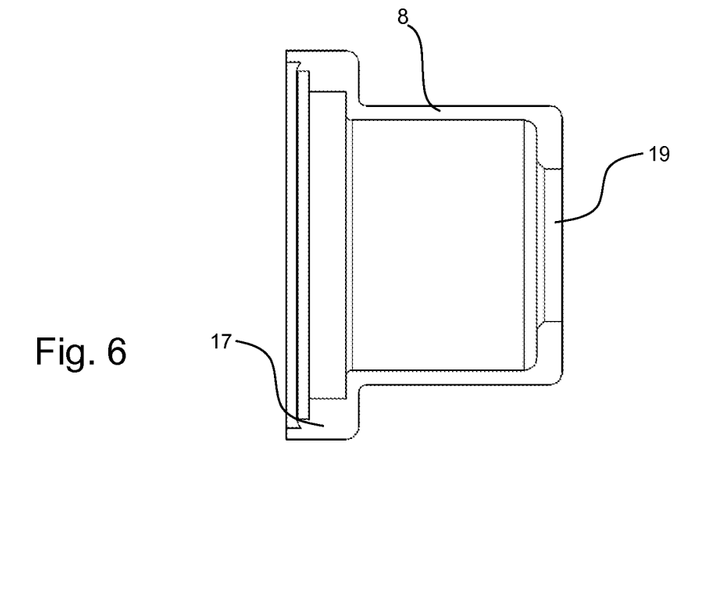
FIG. 6 is a sectional view of the housing of the preferred embodiment of the valve according to the invention.

FIG. 6 is a section view of the housing of the preferred embodiment of the valve according to the invention. Housing 8 has a rather simple structure with a substantially cylindrical shape having openings on both sides wherein second flange 17 which is connected with first component 3 shows a suitable cross-section such that respective attachment means can be applied. Like the first component, the housing 8 is made of a thermoplastic polymer material, preferably ABS.

Figure 7:
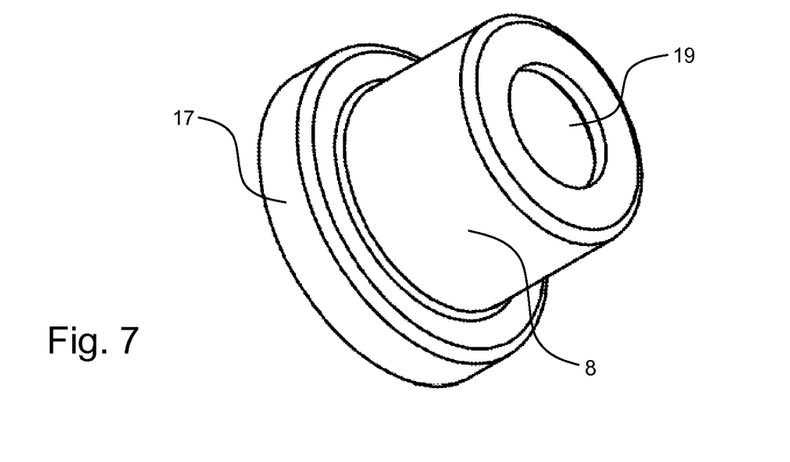
FIG. 7 is a perspective view of the housing of the preferred embodiment of the valve according to the invention.

FIG. 7 is a perspective view of the housing of the preferred embodiment of the valve according to the invention. It shows the opening 19 the dimensions of which are such that second tube 6 may smoothly pass therethrough.

Figure 8:
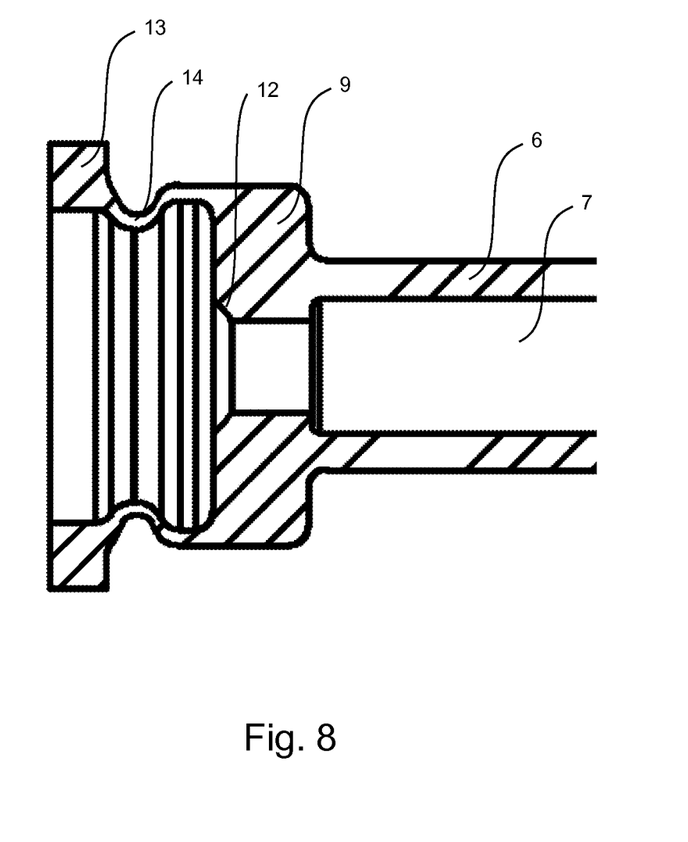
FIG. 8 is a sectional view of the second component used in the preferred embodiment according to the invention.

FIG. 8 is a sectional view of the second component used in the preferred embodiment according to the invention.

Figure 9:
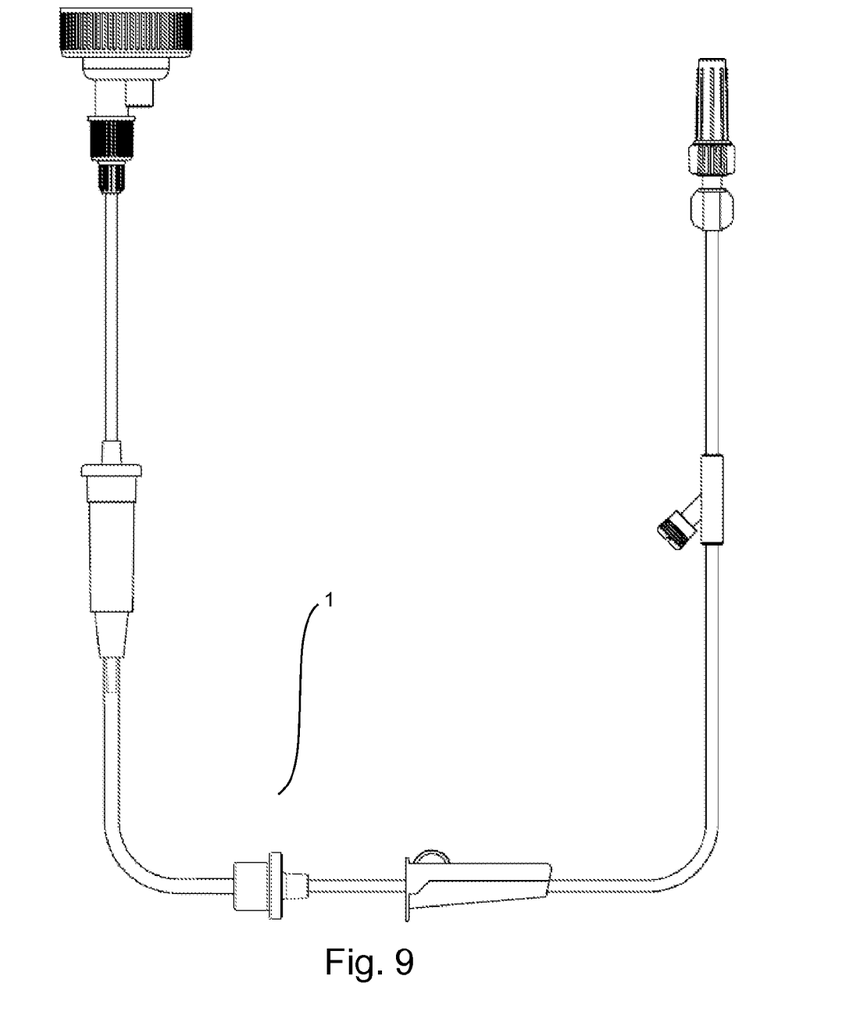
FIG. 9 is a view of an enteral tubing set including the valve according to the present invention.

FIG. 9 shows a top view of an enteral feeding set including the valve according to the invention. On the left-hand side in FIG. 9 are the components in the direction of the container of the enteral nutrition fluid, the other side representing the patient's side. The structure of the enteral feeding set shows that there can be many occasions where one or all of the plurality of silicon tubing portions may be overstretched. The present invention provides a technical solution to prevent a malfunction of the anti-free-flow valve when the tubing is overstretched.

The present invention achieves the objects of the present invention by providing a valve for engagement with a tube used in an enteral feeding or infusion pump, the valve having full anti-free-flow functionality, the valve ensuring a closed state when assembled in a cassette of a enteral feeding or infusion pump, allowing liquids to be pumped through when mounted on a pump, being of simple construction to ensure low manufacturing costs, being small in size, and being compatible with the majority of existing pump devices.

The invention claimed is:

1. A valve for engagement with a tube for use in an enteral feeding or infusion pump for feeding a fluid to a patient, the valve including a first end and a second end opposing the first end and having (a) a first component connectable to a first tube at the first end and having a first cavity and an integral sealing element at a closed end of the first component and (b) a second component separate from and connected to the first component and connectable to a second tube at the second end and having a second cavity, a valve seat and a flexible portion, the sealing element and the valve seat being sealingly engageable to control fluid flow between the first and second tubes, the valve being configured such that applying an axial tension force by moving the second component axially away from the first component brings the valve into an open condition, wherein the flexible portion includes at least one bellows having a spring function in the axial direction, and (c) a housing at least partially covering the second component and configured to operate as a stop limiting the axial movement of the second component.

2. The valve of claim 1 wherein the first component, the second component and the housing are each rotationally symmetric and aligned along a common axis.

3. The valve of claim 1 wherein the first component and the housing are interconnected with one end of the second component firmly engaged therebetween.

4. The valve of claim 3 wherein the first component and the housing are interconnected by mechanical fasteners, welding, or bonding.

5. The valve of claim 4 wherein the first component and the housing are interconnected by ultrasonic welding.

6. The valve of claim 1 wherein the first component and the housing are of a relatively hard thermoplastic polymeric material, and the second component is of a relatively soft elastomeric material.

7. The valve of claim 6 wherein the thermoplastic polymer material is selected from the group of acrylonitrile butadiene styrene (ABS), polypropylene (PP), polyvinyl chloride (PVC), polyethylene (PE), and any combination thereof.

8. The valve of claim 6 wherein the soft elastomeric material is selected from the group of thermoplastic elastomers and silicone rubber.

9. The valve of claim 1 wherein the first component and the housing are each of relatively hard thermoplastic polymer materials such as acrylonitrile butadiene styrene (ABS), polypropylene (PP), polyvinyl chloride (PVC), polyethylene (PE) or any combination thereof.

10. The valve of claim 9 wherein the second component is formed of relatively soft thermoplastic elastomer (TPE) or silicone rubber material.

11. The valve of claim 1 wherein the sealing element has a dome-shaped configuration with a plurality of side channels enabling fluid flow from the first cavity to the second cavity.

12. The valve of claim 11 wherein the valve seat includes a recess for snugly fitting with the dome-shaped sealing element.

13. The valve of claim 1 wherein the second component is integral with the second tube.

14. The valve of claim 1 including a flange to be fitted to a peristaltic pump.

* * * * *

UNITED STATES PATENT AND TRADEMARK OFFICE
CERTIFICATE OF CORRECTION

PATENT NO. : 9,943,681 B2  
APPLICATION NO. : 14/762160  
DATED : April 17, 2018  
INVENTOR(S) : Gagliardoni et al.

Page 1 of 1

It is certified that error appears in the above-identified patent and that said Letters Patent is hereby corrected as shown below:

On the Title Page

In item (72), please correct the name of the last-listed inventor to Jan Willem Marinus Mijers.

Signed and Sealed this  
Fourth Day of December, 2018

Andrei Iancu  
*Director of the United States Patent and Trademark Office*